United States Patent [19]

Suga

[11] 4,125,328

[45] Nov. 14, 1978

[54] APPARATUS FOR MEASURING REFLECTIVITY AND TRANSMISSIVITY OF A SPECIMEN

[76] Inventor: Shigeru Suga, Yoyogi 5-20-2, Shibuya-ku, Tokyo, Japan

[21] Appl. No.: 781,466

[22] Filed: Mar. 25, 1977

[51] Int. Cl.² .................. G01N 21/00; G01N 21/16
[52] U.S. Cl. .................................. 356/73; 356/124; 356/244
[58] Field of Search ............... 356/73, 124, 201, 209, 356/244

[56] References Cited

U.S. PATENT DOCUMENTS

| | | | |
|---|---|---|---|
| 2,869,416 | 1/1959 | Nieman et al. | 356/209 |
| 3,193,690 | 7/1965 | Murata et al. | 356/124 |
| 3,250,177 | 5/1966 | Shack | 356/124 |
| 3,438,713 | 4/1969 | Heynacher et al. | 356/124 |
| 3,771,879 | 11/1973 | Chambu et al. | 356/201 |
| 3,958,882 | 5/1974 | Gast | 356/209 |

Primary Examiner—Vincent P. McGraw

[57] ABSTRACT

An apparatus for measuring reflectivity or transmissivity of a specimen has a source of light fixed to a base, a variable angle specimen frame receiving the light in a narrow beam and transmitting it or reflecting it, a light receiving unit movable around the specimen receiving frame for receiving the transmitted light or the reflected light through an optical template having groups of transverse opaque portions thereacross and movable transversely of the light coming therethrough. A recorder produces a curve of the intensity of light received by the light receiver from which the degree of transmissivity or reflectivity can be determined in comparison with a similar curve for a perfectly transmitting or reflecting specimen.

3 Claims, 9 Drawing Figures

APPARATUS FOR MEASURING REFLECTIVITY AND TRANSMISSIVITY OF A SPECIMEN

The present invention relates to a device for measuring the clarity of an image reflected at varying angles by objects such as metal surfaces and coatings, and measuring the clarity of an image formed by the transmission of light through transparent materials such as plastics and glass.

BACKGROUND OF THE INVENTION AND PRIOR ART

Conventional methods of measuring the clarity of an image have been practiced by observing with the eye black and white striped patterns transmitted through or reflected by the specimen and evaluating the clarity of the transmitted or reflected pattern. With such methods in which the evaluation is based on visual discrimination of the lines in the patterns, however, the values of the clarity always contained errors depending upon the individual observers.

The applicant in the present application has previously invented a method and apparatus for the measurement of the clarity of an image passed through a transparent material (U.S. patent application Ser. No. 683,218 filed Apr. 5, 1976, entitled Method and Apparatus for Measuring the Clearness of an Object) and now abandoned. This method and apparatus, however, is not capable of measuring the clarity of a reflected image.

OBJECTS AND BRIEF SUMMARY OF THE INVENTION

The object of the present invention is to improve the apparatus of the above-described invention for making it possible to measure the clarity of an image transmitted by transparent materials as well as to measure the clarity of images reflected at different angles by a material.

The apparatus of the present invention accurately measures the clarity of an image by means of a photoelectric measuring instrument. In the apparatus, light emitted from a slender tungsten filament lamp is irradiated onto the specimen through a slit lens, either the reflected or the transmitted image of the slit from the specimen is formed on an optical template having vertical stripes or waves thereon by a second lens, and the template is moved so that the change of light corresponding to the number of stripes or waves is received by a light receiving unit and recorded as a light intensity curve. For specimens which transmit or reflect images of good clarity, i.e. those which are perfectly clear or have close to a perfect mirror surface, the amplitude of the curve representing the bright to dark change will be large, while for those specimens which are not clear or do not reflect well, the amplitude of the curve will be small. The reflectivity or transmissivity according to the present invention is found by measuring the maximum value M and the minimum value m of the amplitude of the recorded curve. The more closely spaced the number of stripes or waves on the optical template, the greater the degree to which the clarity can be determined. The number of the stripes or waves can be selected depending upon the specimens which are to be tested.

BRIEF DESCRIPTION OF THE FIGURES

The invention will now be described in greater detail with reference to the accompanying drawings, in which.

DETAILED DESCRIPTION OF THE INVENTION

Figure 1:
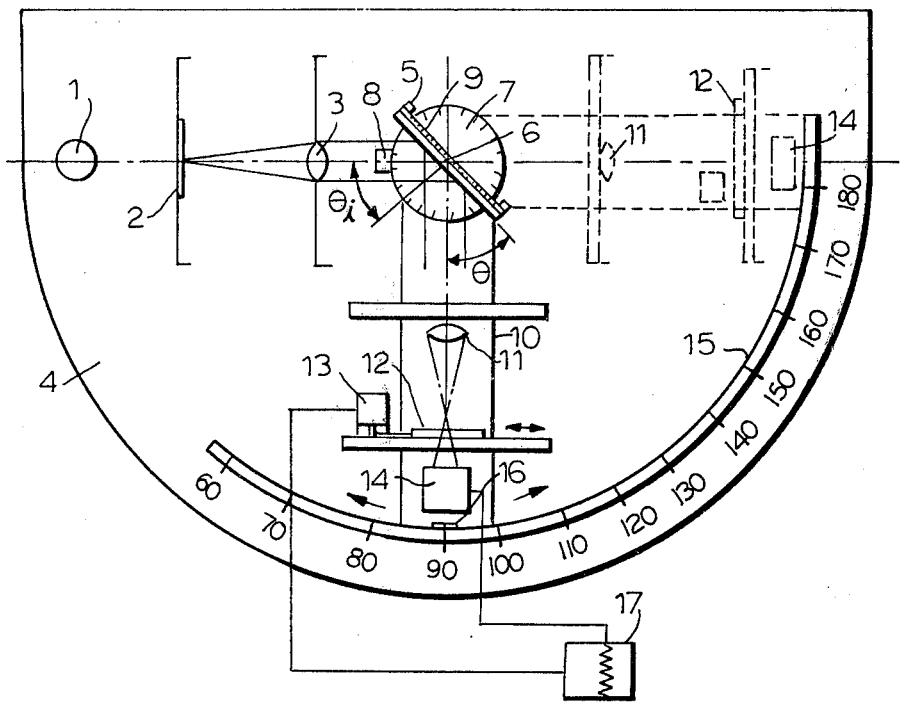
FIG. 1 is a diagram of the apparatus of the present invention.

The apparatus of the invention comprises a source of light fixed to a base, a variable angle specimen frame that varies the incident angle of the light on the specimen, a rotary shaft, a disc with an angular scale on the periphery thereof and rotatable with the specimen frame, a light-receiving unit mounted on the shaft for changing the angle at which light is received from the specimen, and an arc-shaped plate having the periphery graduated in angles and along which the light receiving unit is movable.

As seen in FIGS. 1 and 4–6, the source of light consists of a lamp 1 having a fine tungsten filament, slit forming element 2 and lens 3, and the light source is mounted on the base 4. The light passing through the slit in slit forming element 2 is formed into a parallel beam by the lens 3. A variable angle specimen frame 5 and a disc 7 having an angular scale thereon are mounted for rotation around an axis 6 as a center. The angle between the surface of a specimen 9 mounted in the holder 5 and the light axis of the source of light, i.e. the incident angle $\theta$, is indicated on the scale on disc 7 by an index 8 which is secured on the base 4. The specimen is mounted on the variable angle specimen frame 5 in a manner that the surface of the specimen is positioned on the axis 6.

The light receiving unit consists of a base plate 10, lens 11 mounted thereon, an optical template 12 movably mounted on the base plate 10, optical template moving device 13 for moving the template 12 transversely of the base plate 10, light receiver 14 on the base plate 10, which can be a photo-electric tube and an amplifier, arc-shaped plate 15 having an angular scale thereon and index 16. The arc-shaped plate 15 is mounted on the base 4, and the index 16 is secured on the base plate 10, and the base plate 10 is pivoted at one end on axis 6 and the other end is movable along the inner periphery of the arc-shaped plate 15 with the angle of the base plate 10 relative to the axis of the light source being indicated by index 16. A recorder 17 to record the intensity of light received by receiver 14 is connected to receiver 14.

With the parts in the positions shown in FIG. 1, the light-receiving unit is at an angle of 90° with respect to the axis of the light source, and the specimen holding frame is at an angle of 45° with respect to the axis of the light source, the incident angle $\theta_i$ is 45° with respect to the specimen, and the angle $\theta_r$ of receiving the light from the specimen is 45°. The transmissivity of the specimen can be measured by moving the light receiving unit to a position at 180° with respect to the source of light, i.e. when the light axis of the light-receiving unit aligned with the axis of the light source, as shown by the dotted lines, reference numeral 11' representing the lens, the reference numeral 12' the optical template, and the reference numeral 14' the position of the light-receiver.

To insure that the image of the slit is formed on the optical template, a mirror similar to a perfect mirror, for example and optically excellent glass surface on which a coating of aluminum is deposited, is placed in the specimen holder 5, the angle of incidence of the light and the angle of receiving the light are adjusted, and the reflected light is directed toward the light-receiving unit, and the image is focused on the template by adjusting the lens 11.

When measuring transmissivity, the light image of the slit which has passed through the specimen frame without a specimen therein is focused on the template by the lens 11.

After the adjustment, the specimen is placed in the specimen frame and the image is formed on the template with a degree of clarity, depending on the reflectivity or transmissivity, and light is passed through the optical template. The template is moved transversely to the image of the slit by the moving device 13, and recording paper is fed through the recorder 17 on which a curve corresponding to the intensity of light received from the light receiver 14 is recorded.

The sensitivity of the recorder 17 is so adjusted that the maximum value recorded for completely transmitted or reflected light passed through a transparent part of the optical template is at the full scale, for example 100.

Figure 3:
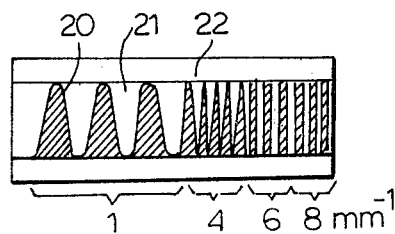
FIG. 3 is a front elevation view of an optical template having projections with a sinusoidally curved profile.
Figure 2:
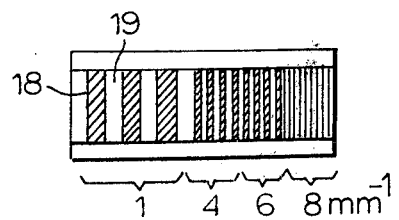
FIG. 2 is a front elevation view of an optical template having vertical stripes.

FIGS. 2 and 3 show optical templates which can be used in the prior art. The optical template of FIG. 2 has opaque vertical stripes 18 which permit no light to pass, and transparent stripes 19. FIG. 3 shows a template having a plurality of opaque spike-shaped projections 20 thereacross, the profiles of which are a sinusoidal curve of a trigonometric function, which permits no light to pass, and having transparent parts 21 therebetween which permit light to pass. The reference numeral 22 designates a frame for the template. In the template, the lines or projections for example, occur with a frequency of 1 mm$^{-1}$, 4 mm$^{-1}$, 6 mm$^{-1}$ and 8 mm$^{-1}$. The measurement can be conducted using either template.

Figure 4:
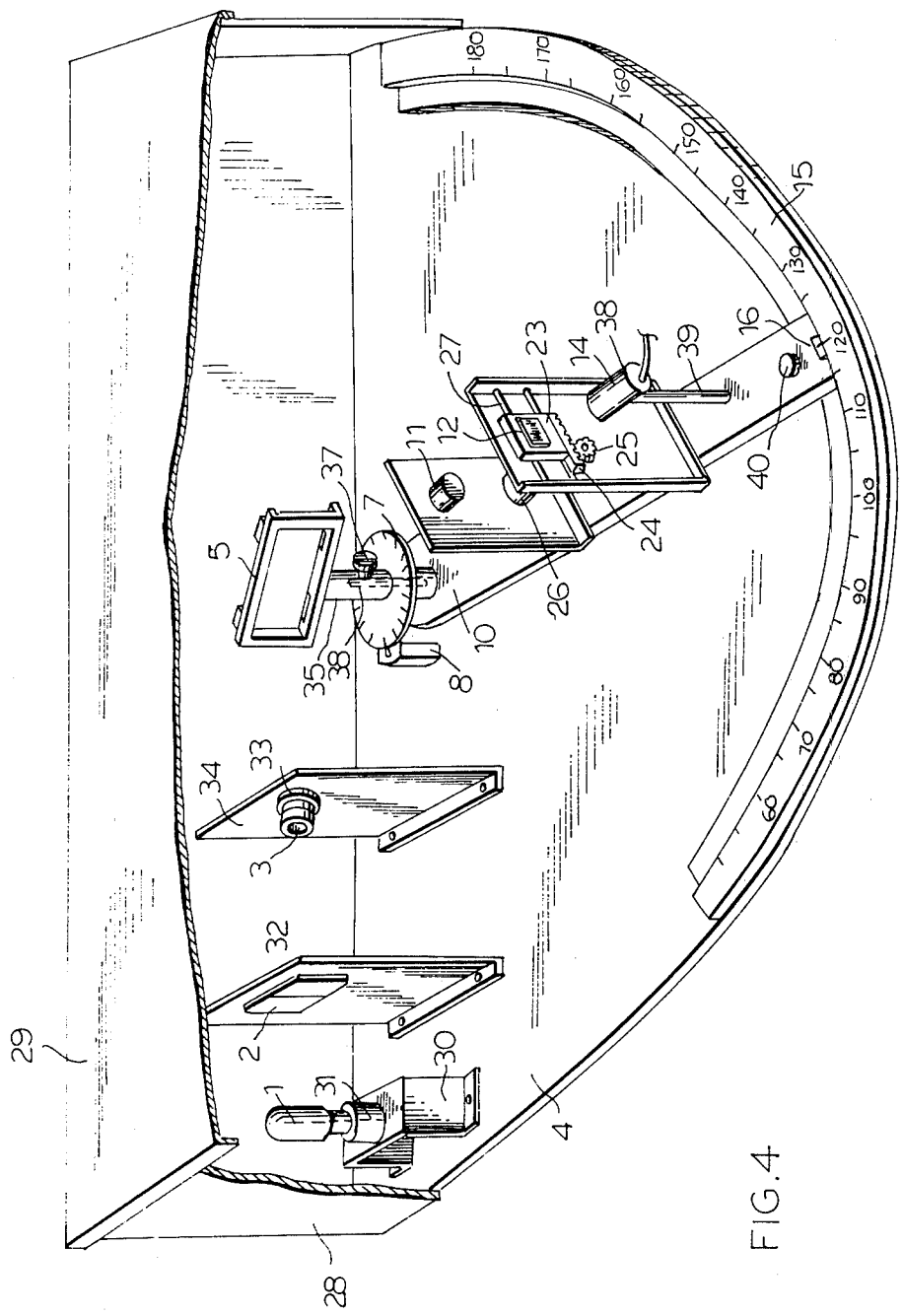
FIG. 4 is a perspective view, partly broken away, of one embodiment of the optical system of the present invention.

As shown in FIG. 4, the optical template moving device 13 consists of a frame 23 which holds the optical template, a rack 24 positioned beneath the frame 23 and on which the frame 23 is mounted, a pinion 26 engaged with the rack 24, a motor 26 driving the pinion 25, and to parallel guide bars 27 along which the frame 23 is driven by the motor 26. The semicircular base 4 has a dark box 28 covering the base and a cover 29 on the box 28 can be opened and closed. The lamp 1 is mounted on a support 30 carrying a socket 31. The slit forming element 2 is mounted on the base 4 on a support fitting 32. The lens 3 is firmly secured on the base by a lens cylinder 33 on a support 34. The lens 3 is adjusted by moving the lens cylinder 33 forward and backward. The variable angle specimen frame 5 is mounted on an outer shaft 35 and the disc 7 is secured thereto, and the outer shaft 35 is rotatable on an inner shaft 36 that is shown in dotted lines. The inner shaft 36 is secured to the base 4. A set screw 37 fixes the position of the variable angle specimen frame so that it will not turn after it has been adjusted. The index 8 which is secured to the base has an index mark thereon on the axis of the light source.

The base plate 10 is mounted so as to turn about the inner shaft 36. The lens 11 having the same construction as the lens 3 is mounted on the light-receiving base plate 10. The light receiver 14 is in a casing 38 which is mounted on the base plate 10 on a metal fitting 39.

Figure 5:
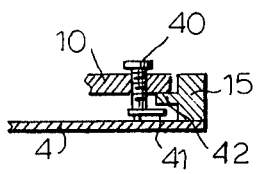
FIG. 5 is a partial sectional view of the engagement of the light-receiving base plate on the apparatus base.

As seen in FIG. 5, a screw 40 is provided for securing the base plate 10 to the arc-shaped plate 15. The screw 40 has a lever 41 attached to the tip thereof, which extends under the inwardly extending projection 42 on the arc-shaped plate 15. When the base plate 10 has been moved to the desired position, the screw 40 is rotated to draw lever 41 up against projection 42, thereby fixing base plate 10 in the desired position.

FIG. 4 shows the parts in positions for measuring reflected light and in which the angle of incidence of the light on the specimen is 60° and the angle of receiving the light is 60°.

Figure 6:
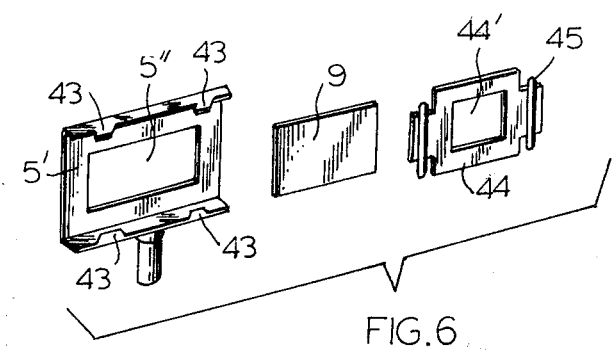
FIG. 6 is an exploded view of a specimen holding frame.

FIG. 6 shows the manner of placing the specimen on the specimen frame. In FIG. 6, the specimen holder has a channel-shaped member 5' having a rectangular hole 5" in the web thereof and four projections 43 projecting inwardly from the flanges thereof. The specimen 9 is placed in the channel-shaped member 5' and is held in position over the hole 5" by a holder plate 44 having a hole 44' therein and leaf springs 45 extending between the projections 43 to hold the specimen in the holder.

Figure 7:
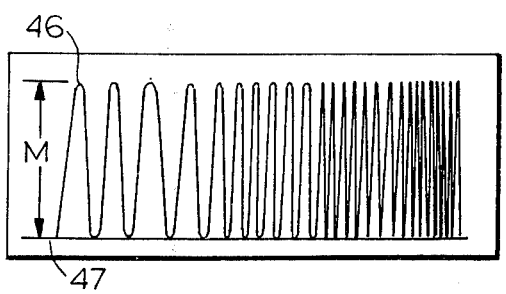
FIG. 7 is a curve of the intensity of light reflected from a perfect mirror surface.

The method of using the device of the present invention for measuring reflectivity and transmissivity will now be described. First, in the case of measuring reflectivity, the light reflected from a perfect mirror surface is measured and recorded. When the template of FIG. 3 is used, the recording obtained is as shown in FIG. 7. Since the specimen has a perfect mirror surface, the image on the template is in focus; the recorded curve resembles the opaque and transparent portions of the template.

The reference numeral 46 designates the full-scale value of transmitted light, and the reference numeral 47 designates the zero value. The amplitude M of the curve can be caused to occupy the full dimension between maximum value of the curve and the zero line by adjusting the sensitivity of said recorder.

If the distance between the minimum value of the curve and the zero line is given by $m$, the value $m$ will be zero since the zero line substantially coincides with the minimum value of the curve.

Figure 8:
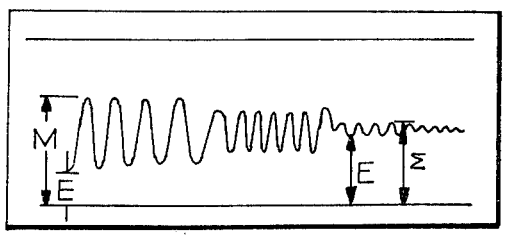
FIG. 8 is a curve similar to FIG. 7 for a specimen having a medium degree of relectivity.

Next, if the reflectivity of a specimen having medium reflectivity is measured, the resulting recording will be as shown in FIG. 8. The curve has an amplitude (M-m) which is less than the value M in the recording shown in FIG. 7. The four parts of the curve correspond to the frequency of stripe or projection occurrence, for example 1, 4, 6 and 8 mm$^{-1}$, on the template from left to right. The portions of the curve having larger frequencies have a smaller amplitude (M-m). This is explained below.

When the image formed on the template is diffused due to poor reflectivity, light passes through neighboring transparent areas, even if the center of the image is positioned on an opaque portion of the template; therefore, the recorded curve representing intensity of the light received by the receiver 14 is not zero.

Similarly, when the center of the image is on the transparent portion due to the movement of the template, the diffused light is interrupted by the neighboring opaque areas and the quantity of light received by the receiver 14 and the value does not reach the full-scale value. Also, if the frequency of opaque portions is large, the light diffuses not just to the neighboring areas, but over a large number of areas. The quantity of light received, as a consequence, is reduced further. Poor reflectivity of the specimen results in small amplitude (M-m), and better reflectivity results in a large amplitude (M-m). A reflectivity ratio $(M-m)/(M+m) \times 100\%$ is conventionally employed to measure transparency. This equation was applied to the measurement of reflectance.

For instance, FIG. 8 shows a curve for a metal plate having a medium degree of reflectivity from which can be found the following degrees of reflectivity:

Example 1

Metal plate, Incident angle 60°, light-receiving angle 60°

| Opaque Portion Frequency | Reflectivity |
| --- | --- |
| 1 mm$^{-1}$ | 45% |
| 4 mm$^{-1}$ | 11% |
| 6 mm$^{-1}$ | 5% |
| 8 mm$^{-1}$ | 1.2% |

Figure 9:
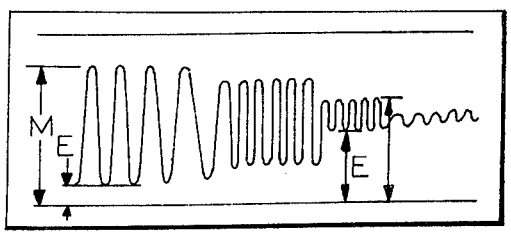
FIG. 9 is a curve similar to FIG. 7 for a specimen having a medium degree of transmissivity.

For measuring transmissivity, the specimen holder is positioned so that the surface of the specimen is positioned at right angles to the light axis of the light source. The recorder is adjusted for the full scale value without a specimen in the specimen holder. The specimen is then placed in the holder and a recording of the light intensity is made. The transmissivity is then found by calculation in the same manner as described above in connection with the measurement of reflectivity. FIG. 9 shows a curve for a plastic plate produced under the conditions in Example 2.

EXAMPLE 2

Plastic Plate

| Opaque Portion Frequency | Degree of Transmissivity |
| --- | --- |
| 1 mm$^{-1}$ | 60% |
| 4 mm$^{-1}$ | 20% |
| 6 mm$^{-1}$ | 10% |
| 8 mm$^{-1}$ | 0% |

FIGS. 7–9 show the results when using a template as shown in FIG. 3. However, the relationships of M, m and reflectivity and transmissivity will be quite the same even when a template having vertical stripes as shown in FIG. 2 is used.

What is claimed is:

1. Apparatus for measuring the reflectivity or transmissivity of a material, comprising:
    a light source means having a tungsten lamp with a fine filament, a slit forming element with a slit therein, and a lens for focusing the light from said slit in said slit forming element into a parallel beam, said lamp, slit forming element and said lens lying in the recited order along a light source axis;
    a specimen holding frame rotatably mounted for pivoting movement around an axis perpendicular to the axis of said light source means, a disc having an angular scale thereon connected to said specimen holding frame, and an index mounted on said light source axis relative to said disc for indicating the angle of light incident on a specimen mounted in said specimen holding frame, said specimen holding frame having specimen holding means thereon for holding a specimen with the surface thereof toward said light source means on said axis of pivoting movement;
    a light receiving unit having a base with one end pivotally mounted for pivoting movement around said axis of pivoting movement of said specimen holding frame, and further having a focusing lens, an optical template and a light receiver mounted on said base on a light receiving axis, said optical template having a plurality of opaque portions extending transversely thereof with transparent portions therebetween, said opaque portions being in at least two groups in which the spacing between the opaque portions is different from the spacing in the other group, said optical template having template moving means coupled thereto for moving the template transversely of the axis of said light receiving means and transversely to the direction of said opaque portions, and said light receiving unit further having a recording means coupled to said light receiver for recording the intensity of light received by said light receiver through said optical template as a continuous curve over a period of time; and
    an arc-shaped plate having an angular scale thereon and extending from a point aligned with the light source axis and on the other side of said specimen holding frame from said light source means to a point at least on a line perpendicular to the light source axis from the axis of pivoting of said specimen holding frame, the end of said light receiving unit base being movable along said arc-shaped plate and having means thereon for fixing said light receiving unit at desired points along said arc-shaped plate.

2. The apparatus as claimed in claim 1 in which said specimen holding frame comprises a channel shaped member having a rectangular aperture in the web portion thereof and a plurality of projections projecting inwardly of said member from the edges of the flanges of said member, and a specimen holding plate having a corresponding aperture therein and slidable into said channel-shaped member and having leaf springs thereon for holding the specimen over said aperture and engagable with said projections for holding the specimen holding plate in said channel-shaped member.

3. The apparatus as claimed in claim 1 in which said light receiving unit further comprises means for holding said optical template having a template holding frame, a pair of parallel bars on which said template holding frame is mounted for sliding movement, a rack on the edge of said template holding frame, and a pinion engaged with said rack and driven by said moving means.

* * * * *